United States Patent [19]

Hijikata

[11] 4,297,199
[45] Oct. 27, 1981

[54] SPECIMEN APPLICATOR

[75] Inventor: Kazuo Hijikata, Hachioji, Japan

[73] Assignee: Olympus Optical Company Limited, Tokyo, Japan

[21] Appl. No.: 210,512

[22] Filed: Nov. 12, 1980

[30] Foreign Application Priority Data

Nov. 14, 1979 [JP] Japan .................................. 54-146386

[51] Int. Cl.³ ............................................ G01N 27/26
[52] U.S. Cl. ............................ 204/299 R; 204/180 S;
204/180 G; 118/224; 118/249; 118/665
[58] Field of Search ............... 204/180 G, 180 S, 299;
118/7, 224, 249

[56] References Cited

U.S. PATENT DOCUMENTS

| 3,839,183 | 10/1974 | Klein et al. | 204/299 R |
| 3,999,505 | 12/1976 | Kato et al. | 118/7 |
| 4,059,501 | 11/1977 | Strickler | 204/299 R |
| 4,130,471 | 12/1978 | Frosch et al. | 204/180 G |
| 4,214,973 | 7/1980 | Nakamura | 204/299 R |
| 4,257,868 | 3/1981 | Arima et al. | 204/299 R |

Primary Examiner—Arthur C. Prescott
Attorney, Agent, or Firm—Haseltine and Lake

[57] ABSTRACT

In applying a specimen to a carrier pre-wetted with an electrolytic solution, the disclosed applicator electrically measures the wetness of the carrier and controls the application of the specimen to the carrier based on the thus detected wetness so as to ensure uniform application of the specimen to the carrier.

5 Claims, 3 Drawing Figures

SPECIMEN APPLICATOR

BACKGROUND OF THE INVENTION

1. Field of the Invention

This invention relates to a specimen applicator, and more particularly to an applicator suitable for an electrophoretic analyzer for apply serum to a carrier wetted with a buffer solution.

2. Description of the Prior Art

A typical electrophoretic analyzer of the prior art includes a wetting station to wet a carrier and a serum-applying station to apply serum on the thus wetted carrier. The wetness of the carrier at the serum-applying station varied depending on the ambient moisture and the operating conditions of wetting rollers at the wetting station, which conditions are susceptible to fluctuations as time elapses. Since the absorption of the serum by the carrier depends on the wetness of the carrier, the serum cannot be applied uniformly when the wetness of the carrier fluctuates. Thus, the electrophoretic analyzer of the prior art has shortcoming in that the accuracy of the analysis tends to be low due to the aforementioned difficulty in achieving the uniform application of the serum.

SUMMARY OF THE INVENTION

Therefore, an object of the present invention is to provide the above referred difficulty and shortcoming of the prior art, by providing an improved specimen applicator which ensures uniform application of a predetermined amount of specimen onto a carrier, so as to facilitate accurate analysis of the specimen.

To fulfill the object, a specimen applicator according to the present invention uses a wetting means to wet a carrier with a certain electrolytic solution, an applying means to apply specimen such as serum onto the thus wetted carrier, a detector to detect electric resistivity of the carrier so as to generate an electric signal representingwetness of the carrier as determined by the thus detected electric resistivity thereof, and a control means to control the application of the specimen onto the carrier based on said electric signal from said detector so as to always apply a certain amount of the specimen to said carrier in a uniform fashion.

BRIEF DESCRIPTION OF THE DRAWINGS

For a better understanding of the invention, reference is made to the accompanying drawings, in which.

DESCRIPTION OF THE PREFERRED EMBODIMENT

Figure 1:
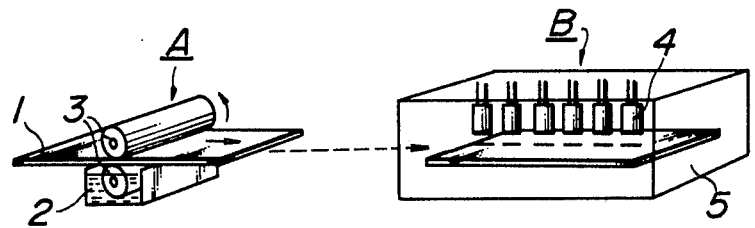
FIG. 1 is a schematic perspective view showing essential portions of an electrophoretic analyzer of the prior art.

Before entering the details of the invention, a typical electrophoretic analyzer of the prior art will be briefly reviewed by referring to FIG. 1. A carrier 1 made of a cellulose acetate membrane or the like is wetted by a buffer solution 2 at a wetting station A having rollers 3 impregnated with the buffer solution. The wetted carrier 1 is forwarded to a serum-applying station B having a plurality of serum applying ends 4. The applying ends 4 are adapted to absorb the serum from a serum vessel (not shown) and apply the absorbed serum onto the carrier so as to form linear tracks of the serum thereon. A cover 5 encloses the serum-applying station B to maintain desired atmospheric conditions therein.

In the conventional electrophoretic analyzer of FIG. 1, the time from the moment when the carrier is wetted at the wetting station A until the applying end 4 comes in contact with the carrier is set at a certain length, and the duration of keeping the applying end 4 in contact with the carrier 1 is also set at a certain length. However, the wetting conditions of the carrier 1 when it is forwarded to the serum-applying station B cannot be kept constant, because the ambient humidity varies and the operative conditions of the wetting rollers 3 at the wetting station A also very as time elapses. Whereby, the ability of the carrier 1 to absorb the serum when the applying ends 4 come in contact with the carrier 1 at the serum-applying station B fluctuates, so that the application of the serum tends to be uneven, resulting in an inaccurate analysis.

The principles of the present invention will now be explained by referring to the graph of FIG. 2. In the graph, the ordinate represents the wetness and the electric resistivity of a carrier, while the abscissa represents the duration of exposing the carrier wetted with a buffer solution in air. The point C of the graph represents the wetness of the carrier which is fully wetted by the buffer solution. If the fully wetted carrier is exposed to air at time $T_0$, the wetness of the carrier becomes smaller as the time elapses. The curves ①,② and ③ show different rates of the wetness reduction depending on the humidity of the air. More particularly, when the humidity of the air is low, the carrier tends to get dried quickly, so that the wetness reduction is also quick as shown by the curve ①. On the other hand, when the humidity of the air is high, the wetness reduction becomes slow as shown by the curve ③.

The carrier is generally made of a thin membrane-like member, e.g., a porous membrane such as a cellulose acetate membrane. Accordingly, when the carrier is dry, its electric resistivity is close to that of electric insulating material, but when the carrier is wetted by a buffer solution which is an electrolyte, the electric resistivity of the carrier is reduced. The point C' of the graph of FIG. 2 shows the electric resistivity of the carrier when being fully wetted by the buffer solution, so that the electric resistivity of the point C' corresponds to the wetness of the point C. If the carrier having the electric resistivity C' is exposed to air at time $T_0$, the electric resistivity of the carrier gradually increases contrary to the variation of the wetness as shown by the curves ①',②', and ③', which curves correspond to the aforementioned wetness reduction curves ①,② and ③. It is noted that the curves ①',②', and ③' are substantially symmetrical relative to the curves ①, ②, and ③ with respect to the line Y of FIG. 2.

Figure 2:
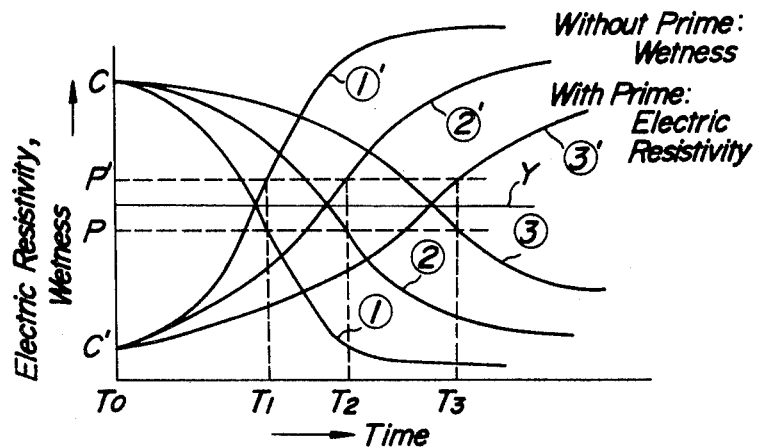
FIG. 2 is a graph showing the relationship between the wetness and electric resistivity of a carrier, to illustrate the principles of the present invention.

If the optimal wetness of the carrier for application of the serum thereon is assumed to be P in FIG. 2, the timing for applying the serum becomes $T_1$, $T_2$, or $T_3$ for the air humidities of the curves ①,② and ③ respectively. On the other hand, the aforementioned wetness P corresponds to the electric resistivity P' of the graph. Thus, the best timing for application of the serum can be determined by detecting the electric resistivity P', and the control of the application of the buffer solution based on the detection of the electric resistivity of the carrier will always ensure uniform application of a certain amount of the serum.

Figure 3:
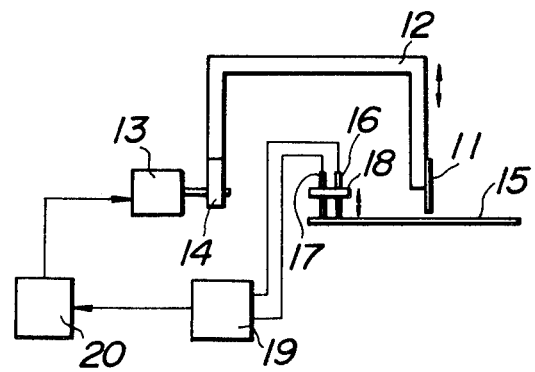
FIG. 3 is a schematic diagram showing the formation of a specimen applicator according to the present invention.

FIG. 3 is a schematic block diagram showing the formation of a specimen applicator according to the present invention. An applying end 11 secured to an arm 12 absorbs and holds the serum to be applied. The arm 12 engages a cam 14 secured to the output shaft of a motor 13, so that the rotation of the cam 14 driven by the motor 13 causes the arm 12 to move vertically together with the applying end 11 secured thereto in such a manner that, when the applying end 11 is at the lowest position thereof, the lower tip of the applying end 11 comes in contact with a carrier 15 wetted by a buffer solution (not shown in FIG. 3). A pair of electrically conductive contact terminals 16 and 17 with a predetermined spacing therebetween are secured to an electrically insulating holder 18. The holder 18 is vertically movable and controlled in such a manner that, when the wetted carrier 15 comes to rest at a certain position of the serum-applying station, the holder 18 descends until the lower tips of the paired contact terminals 16 and 17 held thereby come in contact with the wetted carrier 15. The paired contact terminals 16 and 17 are connected to a resistance sensing-comparing circuit 19. The resistance sensing-comparing circuit 19 applies a predetermined voltage across the paired contact terminals 16 and 17 to cause an electric current to flow through the carrier 15 and senses a voltage drop, e.g., a DC voltage drop, caused by said electric current, which voltage drop corresponds to the electric resistivity of the carrier. At the same time, the circuit 19 compares the thus sensed voltage drop with a reference voltage corresponding to that electric resistivity (the point P' of FIG. 2) which represents the optimal wetness of the carrier for application of the serum. When the aforementioned voltage drop coincides with the aforementioned reference voltage, a coincidence signal is delivered from the circuit 19 to a control circuit 20. The potential applied across the paired contact terminals 16 and 17 can be a DC voltage as described above, or it can be an AC voltage in order to prevent the electrolytic buffer solution to wet the carrier 15 from causing polarization. The control circuit 20 controls the driving action of the motor 13, based on the coincidence signal from the resistance sensing-comparing circuit 19, so as to control the operation of applying the serum to the carrier.

Whereby, the serum can be applied to the carrier 15 when the wetness of the carrier is optimal, so that uniform application of a certain amount of the serum onto the carrier 15 can be always ensured. The control of the application of the serum can be effected in either of the following two ways; namely, a control by keeping the applying end 11 in contact with the carrier 15 to apply the serum thereon until the electric resistivity of the carrier 15 reaches a certain desired value, so as to complete the serum application by separating the applying end 11 from the carrier 15 when the aforementioned desired value of the electric resistivity is reached; or another control by bringing the applying end 11 into contact with the carrier 15 when the electric resistivity of the carrier 15 reaches a certain desired value, so as to keep the applying end 11 in contact with the carrier 15 for a certain predetermined period to apply the serum to the carrier 15. With either of the aforementioned two controls, a certain amount of the serum can be uniformly applied to the carrier 15. However, in the case of the latter control of serum application, it is preferable to let the applying end 11 to absorb the serum immediately before the electric resistivity of the carrier 15 reaches the desired value, in order to prevent the serum held at the tip of the applying end 11 from getting dried.

As described in the foregoing, the present invention provides a specimen applicator which can always apply a certain amount of specimen on a carrier in a uniform fashion, whereby desired analysis of the specimen can be accurately effected.

It should be understood that the present invention is not restricted to electrophoretic analyzers, but the invention can be utilized in a wide variety of apparatuses wherein certain specimens are applied or attached to carriers wetted by an electrolytic solution.

What is claimed is:

1. A specimen applicator comprising a wetting means to wet a carrier with a certain electrolytic solution, an applying means to apply a specimen onto the thus wetted carrier, a detector to detect electric resistivity of the carrier so as to generate an electric signal representing wetness of the carrier as determined by the thus detected electric resistivity, and a control means to control the application of the specimen onto the carrier based on said electric signal from said detector so as to always apply a certain amount of the specimen onto said carrier in a uniform fashion.

2. A specimen applicator as set forth in claim 1, wherein said specimen is serum.

3. A specimen applicator as set forth in claim 1, wherein said control means is adapted to cause said applying means to apply said specimen onto said carrier until the electric resistivity of the carrier reaches a predetermined value.

4. A specimen applicator as set forth in claim 1, wherein said control means is adapted to cause said applying means to start the application of the specimen onto the carrier when the electric resistivity of the carrier reaches a predetermined value and to continue said application for a predetermined period.

5. A specimen applicator as set forth in claim 1, wherein said control means is adapted to cause said applying means to hold said specimen in a manner ready for application to the carrier when the electric resistivity of said carrier reaches a predetermined value.

* * * * *